United States Patent
Smiley et al.

(10) Patent No.: US 8,328,869 B2
(45) Date of Patent: Dec. 11, 2012

(54) ACCOMMODATING INTRAOCULAR LENSES AND METHODS OF USE

(75) Inventors: Terah Whiting Smiley, San Francisco, CA (US); David John Smith, Highland, CA (US); Steven Choi, Mountain View, CA (US); Henry Wu, Belmont, CA (US); John A. Scholl, San Ramon, CA (US); Denise H. Burns, Sunnyvale, CA (US)

(73) Assignee: PowerVision, Inc., Belmont, CA (US)

( * ) Notice: Subject to any disclaimer, the term of this patent is extended or adjusted under 35 U.S.C. 154(b) by 47 days.

(21) Appl. No.: 12/177,857

(22) Filed: Jul. 22, 2008

(65) Prior Publication Data

US 2008/0306588 A1    Dec. 11, 2008

Related U.S. Application Data

(63) Continuation-in-part of application No. 11/646,913, filed on Dec. 27, 2006, now Pat. No. 7,637,947, which is a continuation-in-part of application No. 10/971,598, filed on Oct. 22, 2004, now Pat. No. 7,261,737, which is a continuation-in-part of application No. 10/734,514, filed on Dec. 12, 2003, now Pat. No. 7,122,053, application No. 12/177,857, which is a continuation-in-part of application No. 11/782,474, filed on Jul. 24, 2007, now abandoned, which is a continuation of application No. 11/173,961, filed on Jul. 1, 2005, now Pat. No. 7,247,168, which is a continuation-in-part of application No. 10/971,598, filed on Oct. 22, 2004, now Pat. No. 7,261,737, which is a continuation-in-part of application No. 10/734,514, filed on Dec. 12, 2003, now Pat. No. 7,122,053.

(60) Provisional application No. 60/433,046, filed on Dec. 12, 2002, provisional application No. 60/951,441, filed on Jul. 23, 2007.

(51) Int. Cl.
*A61F 2/16* (2006.01)

(52) U.S. Cl. ........................................ 623/6.13; 623/6.37

(58) Field of Classification Search .................. 623/6.13, 623/6.22, 6.37, 26

See application file for complete search history.

(56) References Cited

U.S. PATENT DOCUMENTS

| | | |
|---|---|---|
| 4,111,995 A | 9/1978 | Nelson |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |

(Continued)

FOREIGN PATENT DOCUMENTS

EP    0898972 A2    3/1999

(Continued)

OTHER PUBLICATIONS

Smiley et al.; U.S. Appl. No. 12/178,565 entitled "Lens delivery system," filed Jul. 23, 2008.

(Continued)

*Primary Examiner* — William H. Matthews
(74) *Attorney, Agent, or Firm* — Shay Glenn LLP

(57) ABSTRACT

Accommodating intraocular lenses containing a flowable media and their methods of accommodation.

7 Claims, 15 Drawing Sheets

U.S. PATENT DOCUMENTS

| | | |
|---|---|---|
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,200,430 A | 4/1993 | Federman |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A * | 2/1996 | Skottun .................. 623/6.13 |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,464,725 B2 | 10/2002 | Skotton |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |

| | | |
|---|---|---|
| 6,926,736 B2 | 8/2005 | Peng et al. |
| 6,935,743 B2 | 8/2005 | Shadduck |
| 6,966,649 B2 | 11/2005 | Shadduck |
| 6,969,403 B2 | 11/2005 | Peng et al. |
| 7,060,094 B2 | 6/2006 | Shahinpoor et al. |
| 7,068,439 B2 | 6/2006 | Esch |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,689 B2 | 7/2007 | Makker et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,416,300 B2 | 8/2008 | Wei et al. |
| 7,453,646 B2 | 11/2008 | Lo |
| 7,494,505 B2 | 2/2009 | Kappelhof et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,988,290 B2 | 8/2011 | Campbell et al. |
| 7,988,292 B2 | 8/2011 | Neal et al. |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0190153 A1 | 9/2004 | Esch |
| 2004/0230203 A1 | 11/2004 | Yaguchi |
| 2005/0021139 A1 | 1/2005 | Shadduck |
| 2005/0119740 A1 | 6/2005 | Esch et al. |
| 2005/0131535 A1 | 6/2005 | Woods |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0010880 A1 | 1/2007 | Esch |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Ben Nun |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0243247 A1 | 10/2008 | Poley et al. |
| 2008/0269887 A1 | 10/2008 | Cumming |
| 2008/0269987 A1 | 10/2008 | Barron et al. |
| 2008/0300680 A1 | 12/2008 | Joshua |
| 2009/0076602 A1 | 3/2009 | Ho et al. |
| 2009/0124773 A1 | 5/2009 | Zhou et al. |
| 2009/0228101 A1 | 9/2009 | Zadno-Azizi |
| 2009/0234449 A1 | 9/2009 | DeJuan, Jr. et al. |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2010/0039709 A1 | 2/2010 | Lo |
| 2010/0063588 A1 | 3/2010 | Park |
| 2010/0131058 A1 | 5/2010 | Shadduck |
| 2010/0324671 A1 | 12/2010 | Shadduck |
| 2010/0324672 A1 | 12/2010 | Esch et al. |
| 2011/0118834 A1 | 5/2011 | Lo et al. |
| 2011/0153015 A1 | 6/2011 | Simonov et al. |
| 2012/0078364 A1 | 3/2012 | Stenger |
| 2012/0179249 A1 | 7/2012 | Coleman |

FOREIGN PATENT DOCUMENTS

| | | |
|---|---|---|
| FR | 2784575 | 4/2000 |
| JP | 02-167157 | 6/1990 |
| JP | 07-044938 | 5/1995 |
| JP | 9294754 | 11/1997 |
| JP | 10-206609 | 8/1998 |
| JP | 11276509 | 10/1999 |
| RU | 1810052 | 4/1993 |

| | | |
|---|---|---|
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/052242 A1 | 6/2004 |
| WO | WO 2004/054471 A3 | 7/2004 |
| WO | WO 2004/072689 A2 | 8/2004 |
| WO | WO 2005/084588 A1 | 9/2005 |
| WO | WO 2006/004707 A2 | 1/2006 |
| WO | WO2006011937 A2 | 2/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |
| WO | WO 2009/100322 A2 | 8/2009 |
| WO | WO 2009/154455 A1 | 12/2009 |

OTHER PUBLICATIONS

Lendlein et al., "Biodegradable, elastic shape-memory polymers for potential biomedical applications", Science; vol. 296; pp. 1673-1676; May 31, 2002.
Lendlein et al., "Shape-memory polymers," Angew. Chem. Int. Ed.; vol. 41; pp. 2034-2057; 2002.
Shadduck, John H.; U.S. Appl. No. 12/347,816 entitled "Intraocular lenses and business methods," filed Dec. 31, 2008.
Gruber et al.; Exhaustive soxhlet extraction for the complete removal of residual compounds . . . ; Journal of Biomedical Materials Research; vol. 53; No. 5; pp. 445-448; Mar. 2000.
Argento et al.; U.S. Appl. No. 12/685,531 entitled "Intraocular Lenses and Methods of Accounting for Capsule Size Variability and Post-Implant Changes in the Eye," filed Jan. 11, 2010.
Esch, Victor; U.S. Appl. No. 12/782,639 entitled "Accommodating Intraocular Lens," filed May 18, 2010.
Shadduck, John H.; U.S. Appl. No. 12/782,644 entitled "Accommodating Intraocular Lens," filed May 18, 2010.
Baughman et al., "Negative poisson's ratios for extreme states fo matter," Science, vol. 288, pp. 1028-2022, Jun. 16, 2000.
Baughman, "Avoiding the shrink," Nature, vol. 425, pp. 667, Oct. 16, 2003.
Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.
Jeon et al., "Shape memory and nonstructure in poly(norbomyl-POSS) copolymers," Polymer International, vol. 49, pp. 453-457, 2000.
Kim et al., "Polyurethanes having shape memory effects," Polymer, vol. 37, No. 26, pp. 5781-5793, 1996.
Lakes et al., "Dramatically stiffer elastic composite materials due to negative stiffness phase?," Journal of the Mechanics and Physics of Solids, vol. 50, pp. 979-1009, 2002.
Lakes et al., "Extreme damping in composite materials with negative-stiffness inclusions," Nature, vol. 410, pp. 565-567, Mar. 29, 2001.
Lakes, "A broader view of membranes," Nature, vol. 414, pp. 503-504, Nov. 29, 2001.
Lakes, "Extreme damping in compliant composites with a negative-stiffness phase," Philosophical Magazine Letters, vol. 81, No. 2, pp. 95-100, 2001.
Lakes, "Extreme damping in composite materials with a negative stiffness phase," Physical Review Letters, vol. 86, No. 13, pp. 2897-2899, Mar. 26, 2001.
Lakes, "Lateral deformations in extreme matter," Science, vol. 288, pp. 1976, Jun. 2000.
Lakes, "Negative poisson's ratio materials," Science, vol. 238, pp. 551, Oct. 23, 1987.
Lakes, "No contractile obligations," Nature, vol. 358, pp. 713-714, 1992.
Li et al., "Crystallinity and morphology of segmented polyurethanes with different soft-segment length," Journal of Applied Polymer Science, vol. 62, pp. 631-638, 1996.
Liu et al., "Thermomechanical characterization of a tailored series of shape memory polymers," Journal of Applied Medical Polymers, vol. 6, No. 2, 2002.
Mather et al., "Strain recovery in POSS hybrid thermoplastics," Polymer Preprints, vol. 41, No. 1, pp. 528-529, 2000.
Metcalfe et al., "Cold hibernated elastic memory foams for endovascular interventions," Biomaterials, vol. 24, pp. 491-497, 2003.
Lakes et al., "Microbuckling instability in elastomeric cellular sollids," J. Materials Science, vol. 28, pp. 4667-4672, 1993.
Takahashi et al., "Structure and properties of shape-memory polyurethane block copolymers," Journal of Applied Polymer Science, vol. 60, pp. 1061-1069, 1996.
Tobushi et al., "Thermomechanical properties of shape memory polymers of polyurethane series and their applications," Journal de Physique IV, Colloque C1, vol. 6, pp. 377-384, 1996.
Wang et al., "Deformation of extreme viscoelastic metals and composites," Materials Science and Enginerring A, vol. 370, pp. 41-49, 2004.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Wyant et al; "Basic Wavefront Aberration Theory for Optical Metrology," Applied Optics and Optical Engineering, vol. XI, 1992:1-13.
Xu et al., "Basic negative poisson's ratio microstructures by soft lithography," Advanced Materials, vol. 11, No. 14, 1999, pp. 1186-1189, 1999.
Your, Jingjong; U.S. Appl. No. 12/034,942 entitled "Polymeric materials suitable for ophthalmic devices and methods of manufacture," filed Feb. 21, 2008.
Your, Jingjong; U.S. Appl. No. 12/177,720 entitled "Lens material and methods of curing with UV light," filed Jul. 22, 2008.
Smiley et al.; U.S. Appl. No. 12/178,304 entitled "Post-implant accommodating lens modification," filed Jul. 23, 2008.
Smiley et al.; U.S. Appl. No. 12/17,565 entitled "Lens delivery system," filed Jul. 23, 2008.
Choi et al.; U.S. Appl. No. 12/178,454 entitled "Systems and methods for testing intraocular lenses," filed Jul. 23, 2008.
Hildebrand et al.; U.S. Appl. No. 12/872,314 entitled "Lens Capsule Size Estimation," filed Aug. 31, 2010.
Conlisk, A. T. et al; Mass Transfer and Flow in Electrically Charged Micro- and Nano-channels; Analytical Chemistry, vol. 74; iss. 9; pp. 2139-2150; 2002.
Dubbelman et al.; The Thickness of the Aging Human Lens Obtained from Corrected Scheimpflug Images; Optometry & Vison Science; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Vass et al.; Prediction of pseudophakic capsular bag diameter based on biometric variables; J Cataract Refract Surg.; vol. 25; pp. 1376-1381; 1999.
Anvar et al.; U.S. Appl. No. 13/033,474 entitled "Fluid for Accommodating Intraocular Lenses," filed Feb. 23, 2011.
Scholl et al.; U.S. Appl. No. 13/193,487 entitled "Accommodating Intraocular Lenses," filed Jul. 28, 2011.
Smiley et al.; U.S. Appl. No. 13/193,983 entitled "Accommodating Intraocular Lenses," filed Jul. 29, 2011.
Smiley et al.; U.S. Appl. No. 13/194,004 entitled "Accommodating Intraocular Lenses," filed Jul. 29, 2011.

Hildebrand et al.; U.S. Appl. No. 13/180,427 entitled "Intraocular lens delivery devices and methods of use," filed Jul. 11, 2011.

Shadduck, John H.; U.S. Appl. No. 13/300,245 entitled "Accommodating Intraocular Lenses and Methods of Use," filed Nov. 18, 2011.

Matthews, Gregory V.; U.S. Appl. No. 13/427,617 entitled "Intraocular Lens Loading Systems and Methods of Use," filed Mar. 22, 2012.

USPTO, "Office Action," corresponding U.S. Appl. No. 12/782,639, mailed on Jan. 9, 2012, 33 pages.

USPTO, "Office Action," corresponding U.S. Appl. No. 12/853,892, mailed on Jan. 9, 2012, 31 pages.

* cited by examiner

ACCOMMODATING INTRAOCULAR LENSES AND METHODS OF USE

CROSS-REFERENCE TO RELATED APPLICATIONS

This application is a continuation-in-part of U.S. application Ser. No. 11/646,913, filed Dec. 27, 2006 (now U.S. Pat. No. 7,637,947); which is a continuation-in-part of U.S. application Ser. No. 10/971,598, filed Oct. 22, 2004 (now U.S. Pat. No. 7,261,737); which is a continuation-in-part of U.S. application Ser. No. 10/734,514, filed Dec. 12, 2003 (now U.S. Pat. No. 7,122,053); which claims the benefit of U.S. Provisional Application No. 60/433,046, filed Dec. 12, 2002, each of which is hereby incorporated by reference herein.

This application is also a continuation-in-part of U.S. application Ser. No. 11/782,474, filed Jul. 24, 2007 (now abandoned); which is a continuation of U.S. application Ser. No. 11/173,961, filed Jul. 1, 2005 (now U.S. Pat. No. 7,247,168); which is a continuation-in-part of U.S. application Ser. No. 10/971,598, filed Oct. 22, 2004 (now U.S. Pat. No. 7,261,737); which is a continuation-in-part of U.S. application Ser. No. 10/734,514, filed Dec. 12, 2003 (now U.S. Pat. No. 7,122,053); which claims the benefit of U.S. Provisional Application No. 60/433,046, filed Dec. 12, 2002; each of which is hereby incorporated by reference herein.

This application also claims the benefit of U.S. Provisional Application No. 60/951,441, filed Jul. 23, 2007, which is incorporated herein by reference in its entirety.

BACKGROUND OF THE INVENTION

Cataracts are a major cause of blindness in the world and the most prevalent ocular disease. When the disability from cataracts affects or alters an individual's activities of daily living, surgical lens removal with intraocular lens ("IOL") implantation is the preferred method of treating the functional limitations.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an IOL. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule, also referred to herein as "capsular sac," supported by the ciliary muscles via zonules, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein) move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles via the zonules cause the lens to change shape.

Isolated from the eye, the relaxed capsule and lens take on a more spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although efforts have been made with accommodating IOLs, there is a need for an accommodating IOL that can restore as much accommodation to the eye as possible.

SUMMARY OF THE INVENTION

One aspect of the invention is an accommodating intraocular lens. The lens includes an optic portion comprising an anterior element, a posterior element, and an intermediate layer disposed along an optical path of the lens, wherein the intermediate layer is disposed between the anterior element and the posterior element. The lens also includes a peripheral portion in fluid communication with the optic portion. The intraocular lens is adapted such that when a flowable media is moved between the peripheral portion and the optic portion in response to ciliary muscle movement, at least two of the anterior element, the posterior element, and the intermediate layer move from a first configuration to a second configuration.

In some embodiments the posterior element comprises a channel formed therein, and wherein the posterior element and the intermediate layer define an active channel in fluid communication with the peripheral portion. The anterior element can be bonded to the intermediate layer, such as along the periphery of the anterior layer. The intermediate layer can also be bonded to the posterior element.

In some embodiments the intermediate layer comprises an actuator. The actuator can be in contact with the anterior element throughout an entire accommodation range of the intraocular lens, or the actuator may not be in contact with the anterior element throughout an entire accommodation range of the intraocular lens. The actuator assumes a substantially conical configuration in a disaccommodated configuration.

In some embodiments the peripheral portion is coupled to the posterior element. The posterior element can include a buttress element disposed at the periphery of the posterior element, and wherein the peripheral portion is coupled to the buttress element. The peripheral portion can comprises a haptic and the haptic comprises a connection element adapted to fit within a bore in the buttress element. The peripheral portion can comprise a haptic and the buttress element comprises a connection element adapted to fit within a bore in the haptic.

In some embodiments the intermediate layer and the anterior element define a passive chamber containing a second flowable media therein. The anterior element, the intermediate layer, the posterior element, the second flowable media, and the flowable media can all be substantially indexed matched to one another.

In some embodiments the at least two of the anterior element, the posterior element, and the intermediate layer that move from a first configuration to a second configuration are the intermediate layer and the anterior element.

One aspect of the invention is an accommodating intraocular lens. The lens includes an optic portion comprising an anterior element, a posterior element, and an intermediate layer disposed between the anterior element and the posterior element. An anterior surface of the anterior element defines an anterior surface of the lens and a posterior surface of the posterior element defines a posterior surface of the lens. The lens also includes a peripheral portion in fluid communication with the optic portion. The intraocular lens is adapted such that when a flowable media is moved between the optic portion and the peripheral portion in response to ciliary muscle movement, at least one of the anterior surface of the lens and the posterior surface of the lens moves from a first configuration to a second configuration.

In some embodiments a first surface of the intermediate layer partially defines an active channel which is in fluid communication with the peripheral portion. The intermediate layer and the posterior element can define the active channel. The intermediate layer and the anterior element can define a passive chamber containing a second flowable media. In some embodiments the anterior element, the posterior element, the intermediate layer, the flowable media, and the second flowable media all are substantially index-matched to each other.

In some embodiments the anterior element is bonded to the intermediate layer, which can be along the periphery of the anterior layer. The intermediate layer can be bonded to the posterior element.

In some embodiments the intermediate layer comprises an actuator, which can be in contact with the anterior element throughout an entire accommodation range of the intraocular lens, or which can be in contact with the anterior element only through a portion of an entire accommodation range of the intraocular lens. The actuator can assume a substantially conical configuration in a disaccommodated configuration.

In some embodiments the peripheral portion is coupled to the posterior element. The posterior element can include a buttress element disposed at the periphery of the posterior element, and the peripheral portion is coupled to the buttress element. The peripheral portion can comprises a haptic and the haptic comprises a connection element adapted to fit within a bore in the buttress element. The buttress element can alternatively comprise a connection element adapted to fit within a bore in the haptic.

One aspect of the invention is a method of changing an optical parameter of an accommodating intraocular lens. The method includes providing an intraocular lens comprising an optic portion and a peripheral portion extending peripherally from the optic portion, wherein the optic portion comprises an anterior element, a posterior element, and an intermediate layer disposed between the anterior element and the posterior element. The optic portion and the peripheral portion are in fluid communication. The method also includes moving a flowable media between the optic portion and the peripheral portion in response to ciliary muscle movement to change an optical parameter of the intraocular lens, wherein moving a flowable media between the optic portion and the peripheral portion comprises moving at least two of the anterior element, the intermediate layer, and the posterior element from a first configuration to a second configuration.

In some embodiments moving a flowable media between the optic portion and the peripheral portion comprises deforming the peripheral portion. Moving at least two of the anterior element, the intermediate layer, and the posterior element can comprise moving the intermediate layer and the anterior element from a first configuration to a second configuration.

In some embodiments the intermediate layer and the posterior element define an active channel in fluid communication with the peripheral portion, and the intermediate layer and the anterior element define a passive chamber containing a second flowable media therein. The method further comprising index matching the anterior element, the intermediate layer, the posterior element, the second flowable media, and the flowable media.

One aspect of the invention is a method of changing the power of an accommodating intraocular lens. The method includes providing an intraocular lens including an optic portion and a non-optic peripheral portion, wherein the optic portion comprises an anterior element, a posterior element, and an intermediate layer disposed between the anterior element and the posterior element, and wherein an anterior surface of the anterior element defines an anterior surface of the intraocular lens, and wherein a posterior surface of the posterior element defines a posterior surface of the intraocular lens. The method also includes moving a flowable media between the optic portion and the non-optic portion in response to ciliary muscle movement to change the power of the intraocular lens, wherein moving a flowable media between the optic portion and the non-optic portion comprises moving at least one of the anterior surface of the intraocular lens and the posterior surface of the intraocular lens.

In some embodiments moving a flowable media between the optic portion and the non-optic portion comprises deforming the non-optic portion. Moving a flowable media between the optic portion and the non-optic portion can comprise moving the intermediate layer from a first configuration to a second configuration.

In some embodiments the intermediate layer and the posterior element define an active channel in fluid communication with the peripheral portion, and the intermediate layer and the anterior element define a passive chamber containing a second flowable media therein. The method also includes index matching the anterior element, the intermediate layer, the posterior element, the second flowable media, and the flowable media.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The invention relates generally to intraocular lenses ("IOLs") and particularly to accommodating intraocular lenses. In preferred embodiments the IOL includes a flowable media (such as a fluid, gelatinous material, etc.) that is moved within the IOL, in response to ciliary muscle movement, to change the power of the IOL.

Figure 1:
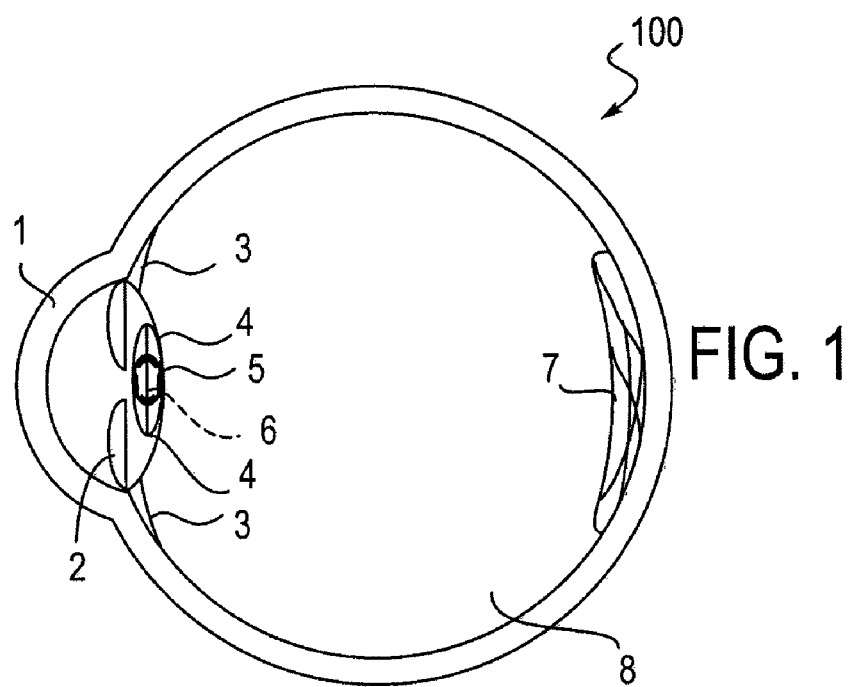
FIGS. 1, 2A, and 2B illustrate the structure and operation of a human eye.

FIGS. 1 and 2 illustrate the structure and operation of a human eye. Eye 100 includes cornea 1, iris 2, ciliary muscles 3, ligament fibers or zonules 4, capsule 5, lens 6 and retina 7. Natural lens 6 is composed of viscous, gelatinous transparent fibers, arranged in an "onion-like" layered structure, and is disposed in transparent elastic capsule 5. Capsule 5 is joined by zonules 4 around its circumference to ciliary muscles 3, which are in turn attached to the inner surface of eye 0. Vitreous 8 is a highly viscous, transparent fluid that fills the center of eye 100.

Figure 2A:
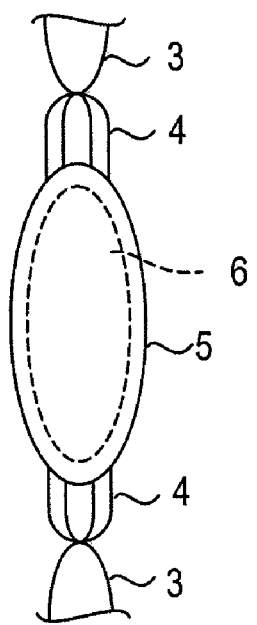
Figure 2B:
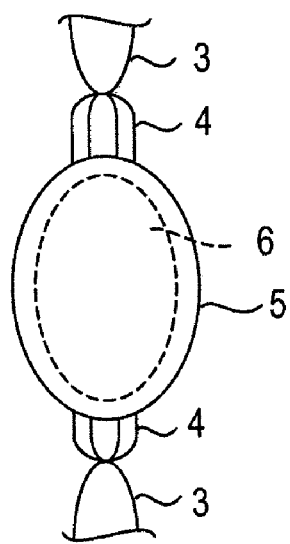

Isolated from the eye, the relaxed capsule and lens take on a convex shape. However, when suspended within the eye by zonules 4, capsule 5 moves between a moderately convex shape (when the ciliary muscles are relaxed) and a highly convex shape (when the ciliary muscles are contracted). As shown in FIG. 2A, when ciliary muscles 3 relax, capsule 5 and lens 6 are pulled about the circumference, thereby flattening the lens. As shown in FIG. 2B, when ciliary muscles 3 contract, capsule 5 and lens 6 relax and become thicker. This allows the lens and capsule to assume a more convex shape, thus increasing the diopter power of the lens.

Additionally, various natural mechanisms affect the design requirements of the present invention. For example, during accommodation the pupil naturally stops down (i.e., reduces in diameter) which reduces the area of the natural lens that transmits light. In addition, the eye will experience the Stiles-Crawford Effect which also reduces the effective area of the natural lens. In particular, the brightness of light rays incident on cones in the eye is dependent on the angle at which those rays are incident on the cones. In particular, light rays that strike the cones perpendicular to their surface appear brighter than those that do not. As a result, the light rays passing through the periphery of the lens are less significant for proper vision.

Figure 3:
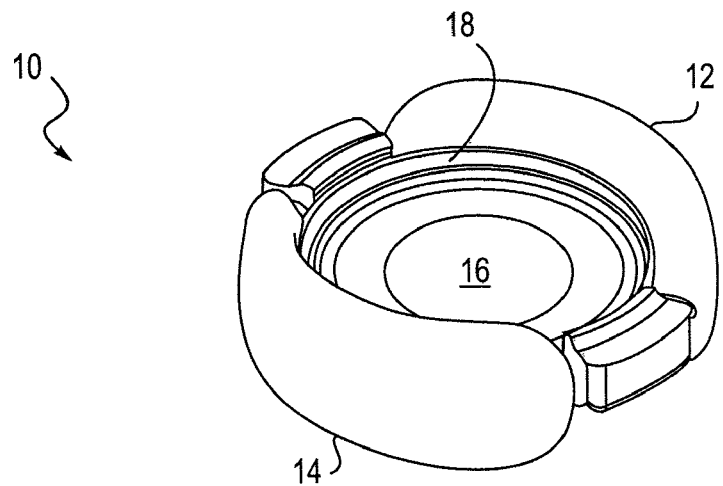
FIGS. 3-5 show an exemplary embodiment of an intraocular lens.
Figure 4:
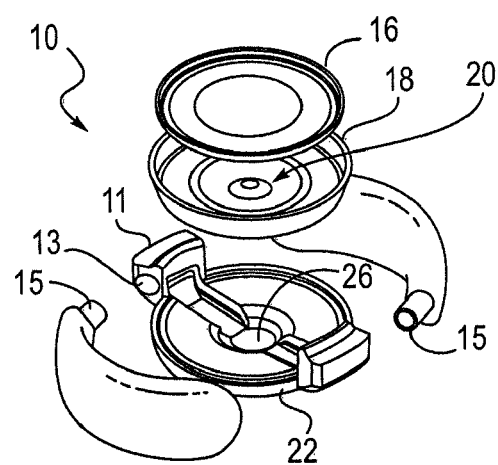
Figure 5:
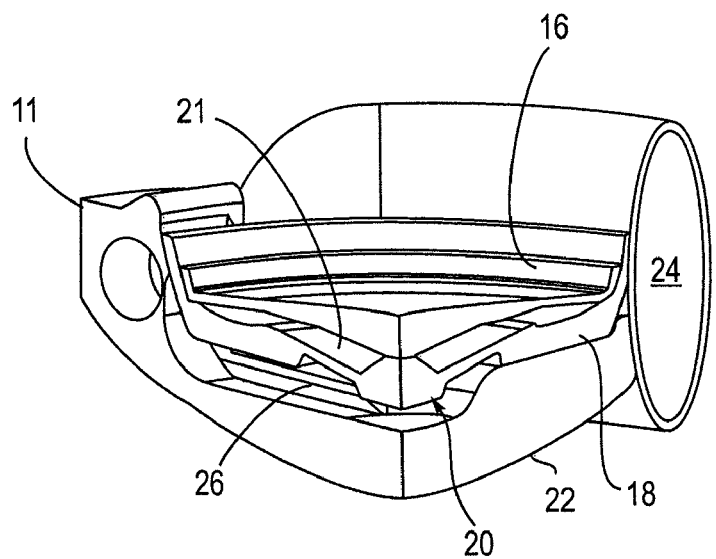

FIGS. 3-5 show a first embodiment of accommodating IOL 10. IOL 10 includes a peripheral non-optic portion comprising haptics 12 and 14. The IOL also includes an optic portion including anterior lens element 16, intermediate layer 18 which comprises actuator 20, and substrate, or posterior element, 22. Anterior element 16 is bonded to intermediate layer 18 at its periphery. In some embodiments the anterior element may also be bonded to actuator 20. The intermediate layer is also bonded to posterior element 22. The inner surface of haptics 12 and 14 define interior volumes 24 which are in fluid communication with active channel 26 defined by posterior element 22 and intermediate layer 18. As shown, actuator 20 is integral with intermediate layer 18. Posterior element 22 is molded with buttresses 11 which include a buttress bore 13 therethrough. The haptics have a haptic attachment element 15 (which can be stiff or flexible) which is sized and shaped to fit within buttress bore 13. An adhesive layer can be applied to the outer surfaces of the haptic attachment elements and/or the inner surface of the buttress bore to facilitate attachment of the haptics to the optic portion. The IOL contains a flowable media within the haptics and the active channel. The IOL also includes passive chamber 21 that is defined by the anterior element and the intermediate layer. The passive chamber contains a second flowable media (e.g., a fluid, elastomer, etc.), which may be the same as the fluid within the haptics and active channel, or it may be a different flowable media. The active channel and the passive chamber are not in fluid communication.

Deformation of haptics 12 and 14 in response to contraction of ciliary muscles movement transfers the flowable media (such as a fluid) between interior volume 24 and active channel 26. When the flowable media is transferred into the active channel from the haptics, the pressure in the active channel increases, causing actuator 20 to deflect in the anterior direction. This causes anterior element 16 to deflect in the anterior direction, increasing the IOL power in this accommodated configuration.

In any of the embodiments herein, moving fluid between the haptics and the optic portion can cause the change in curvature of the posterior element rather than, or in addition to, the anterior element. While changing the curvature of the anterior element is described herein, this is not meant to be limiting to the IOLs. For example, the IOL can be flipped upon implantation such that the anterior element is disposed on the posterior side of the lens, while the posterior element is disposed on the anterior side of the lens. Moving fluid from the haptics to the optics would therefore cause the posterior surface of the IOL deflect. Alternatively, the actuator can be in contact with the posterior element and the active channel can be defined by the intermediate layer and the anterior element, while the passive chamber is defined by the posterior element and the intermediate layer. Moving fluid from the haptics to the active channel would thereby deflect the posterior element.

Figure 6:
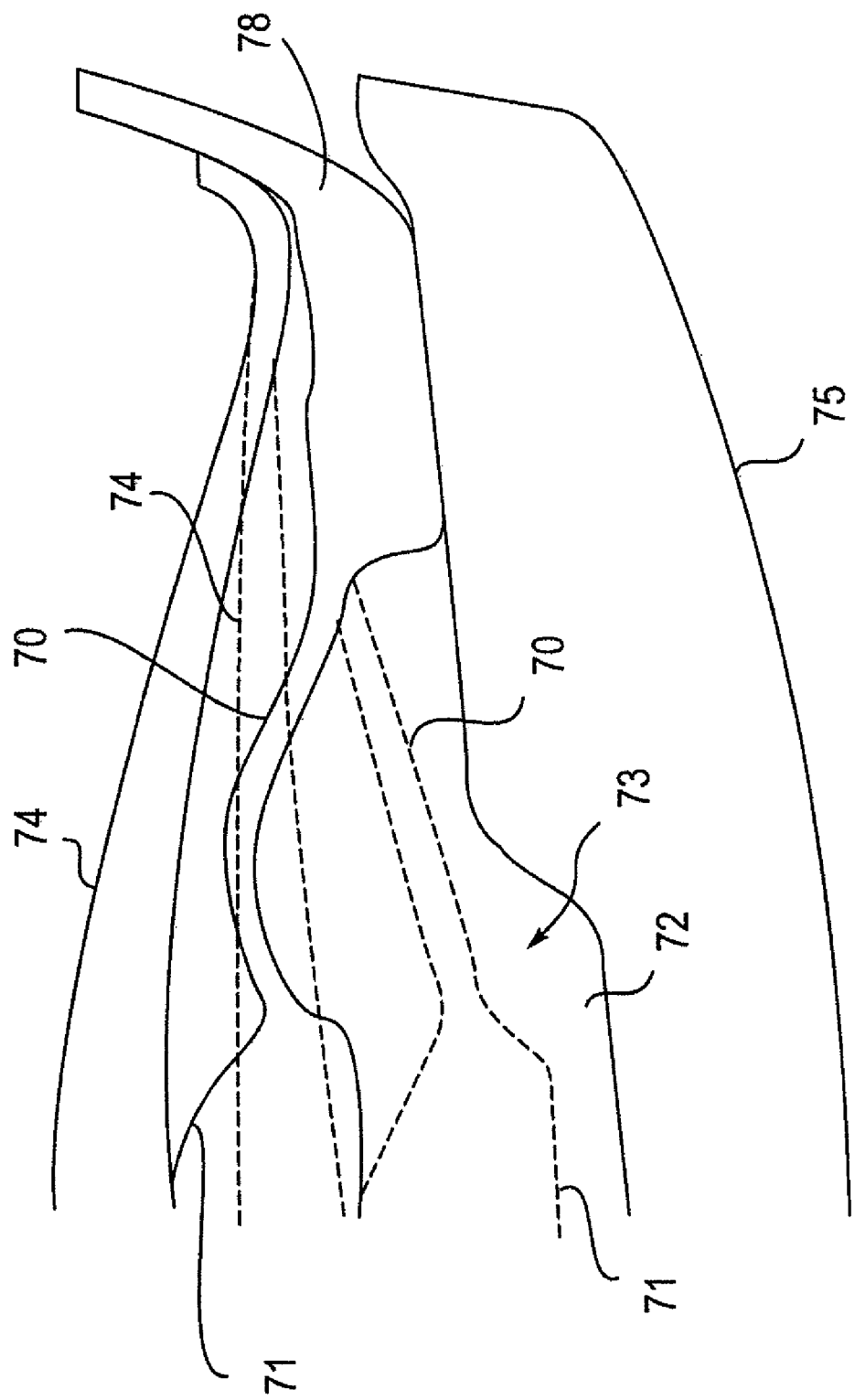
FIG. 6 shows a portion of an exemplary intraocular lens in disaccommodative and accommodative configurations.

FIG. 6 is a cross sectional view of a section of an exemplary IOL showing the IOL in a disaccommodated state (dashed lines) and an accommodated state (solid lines). The IOL includes anterior element 74, intermediate layer 78 which includes actuator 73, and posterior element 75. Actuator 73 is comprised of deflection element 71 and bellows 70. When the pressure is increased in active channel 72, bellows 70 change configuration from the generally conical shape of the disaccommodated state to a curvilinear configuration of the accommodated state. Deflection element 71 is forced in the anterior direction due to the increase in pressure. This causes anterior element 74 to deflect in the anterior direction as well, steepening the curvature of the anterior element and thereby increasing the power of the lens.

All of the components of the optic portion, including the active flowable media and the passive flowable media, can be substantially index-matched to provide for a generally singular lens element defined by the anterior surface of the anterior element and the posterior surface of the posterior element. "Substantially index-matched" as used herein refers to an IOL whose components are intended to have the same index of refraction, but whose actual indices may differ slightly. The term also refers to a lens which can have adhesive (to bond different components of the lens together) which may have an index of refraction that is slightly different than the indices of the other IOL components.

Some of the components may, however, have different indices of refraction, creating additional interfaces within the IOL.

Figure 7:
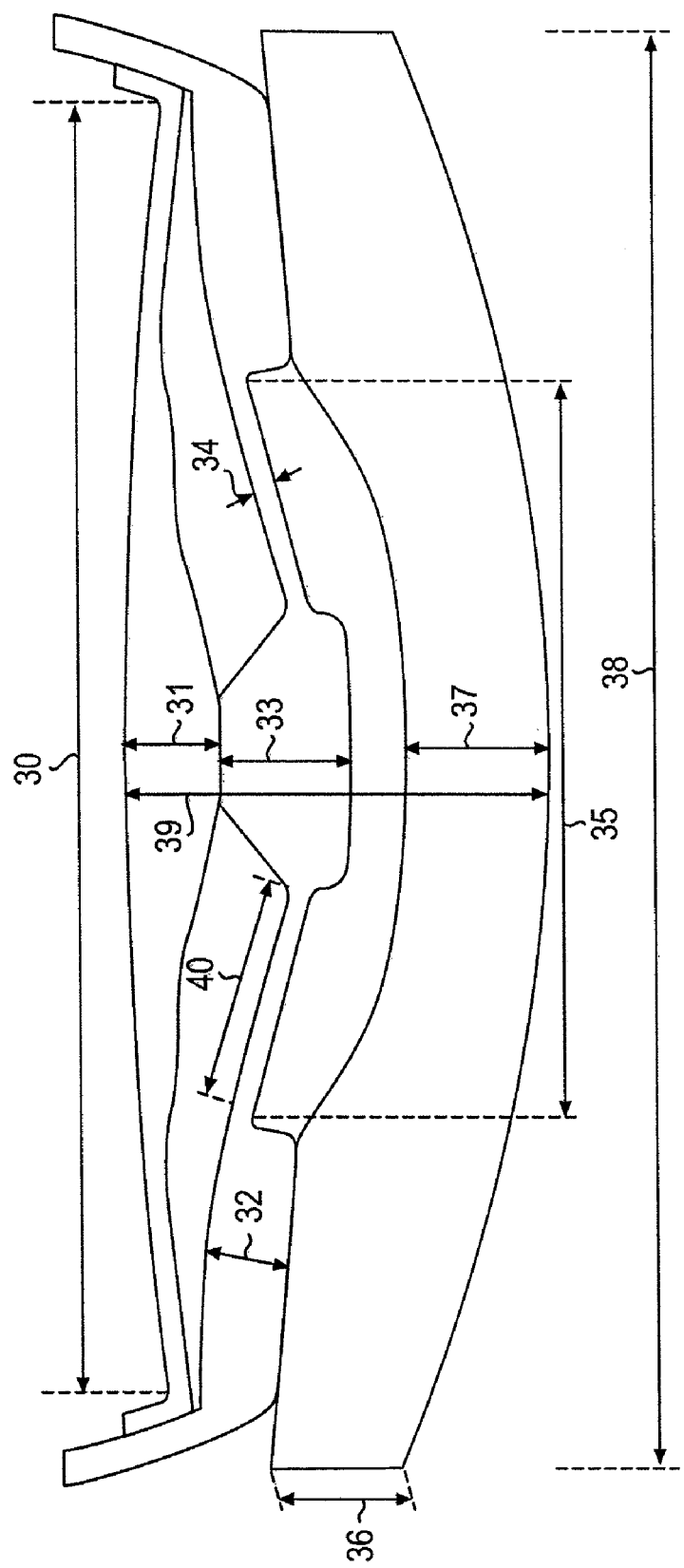
FIG. 7 shows an exemplary optic portion of an intraocular lens.

FIG. 7 is a cross sectional view of an IOL (haptics not shown) similar to that shown in FIGS. 3-5. FIG. 7 illustrates exemplary dimensions of the optic portion of the IOL. Anterior element diameter 30 is about 6.0 mm. The anterior element thickness 31 at the center of the anterior element is about 0.43 mm. Intermediate layer edge thickness 32 is about 0.35 mm. Intermediate layer center thickness 33 (i.e., deflection element center thickness) is about 0.63 mm. Bellows length 40 is about 1.0 mm. Bellows thickness 34 is about 0.10 mm. Actuator diameter 35 is about 3.40 mm. Posterior element edge thickness 36 is about 0.60 mm. Posterior element center thickness 37 is about 0.70 mm. Posterior element diameter 38 can be about 6.6 mm to about 7.4 mm. The IOL center thickness 39 (in the disaccommodated configuration) between the anterior surface of the anterior element and posterior surface of the posterior element along the optical axis of the lens is about 1.8 mm to about 2.2 mm.

Bellows thickness 34 can be adjusted to change the responsiveness of the actuator. As the thickness of the bellows decreases, less fluid pressure is generally required to displace the actuator. In some embodiments the bellows thickness is between about 0.05 mm and about 0.3 mm.

Decreasing the anterior element thickness 31 generally increases the responsiveness of the actuator for a given fluid pressure. Length of bellows 40 can also be adjusted to alter the responsiveness of the actuator (actuator diameter 35 can similarly be adjusted). As the length of the bellows increases, the volume of the active channel is increased and more volume of flowable media is required to move the actuator. However, by increasing the bellows length, the pressure in the active channel is decreased. Therefore, the volume and pressure required to drive the actuator can be optimized in combination with the flowable media transferred from the haptics to provide the greatest response.

In some embodiments the length of the bellows is between about 1 mm and 2 mm. In some embodiments actuator diameter 35 is between about 2.8 mm and about 4.2 mm.

The dimensions given above are merely exemplary and not intended to be limiting.

Figure 8A:
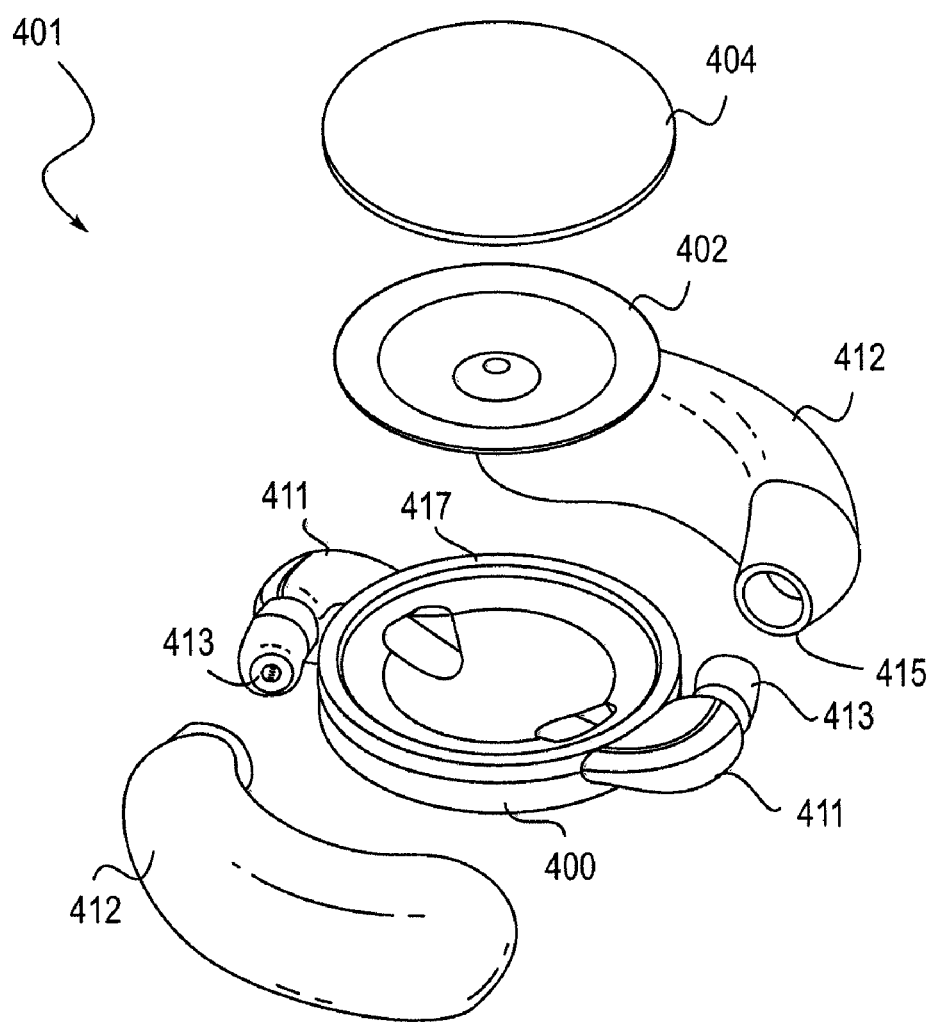
FIGS. 8A-8C show an alternative embodiment of an intraocular lens.
Figure 8B:
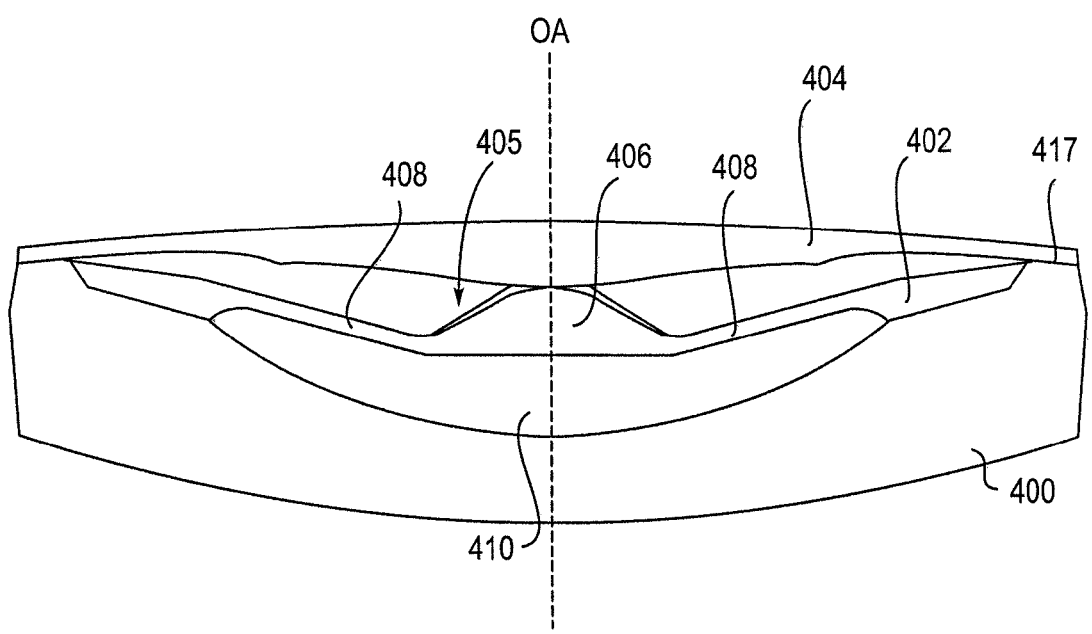
Figure 8C:
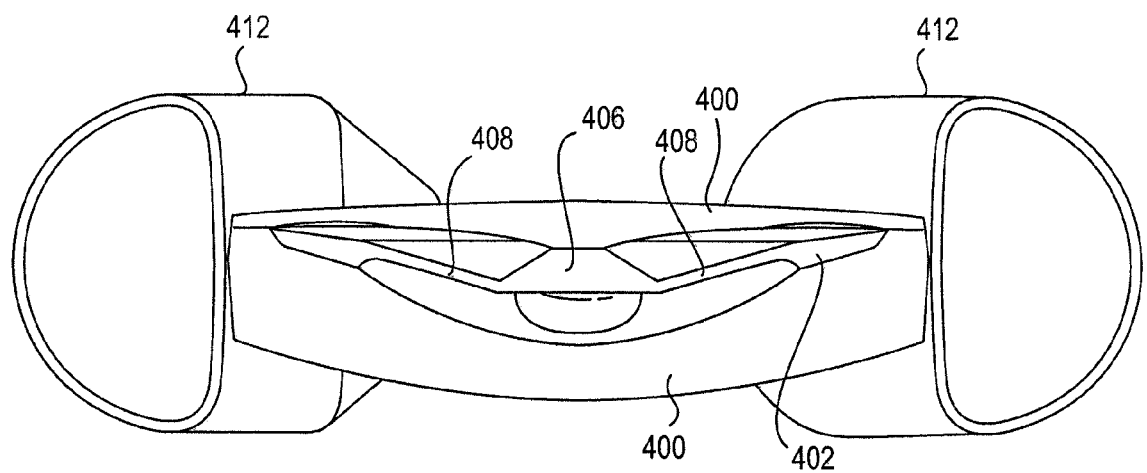
Figure 9:
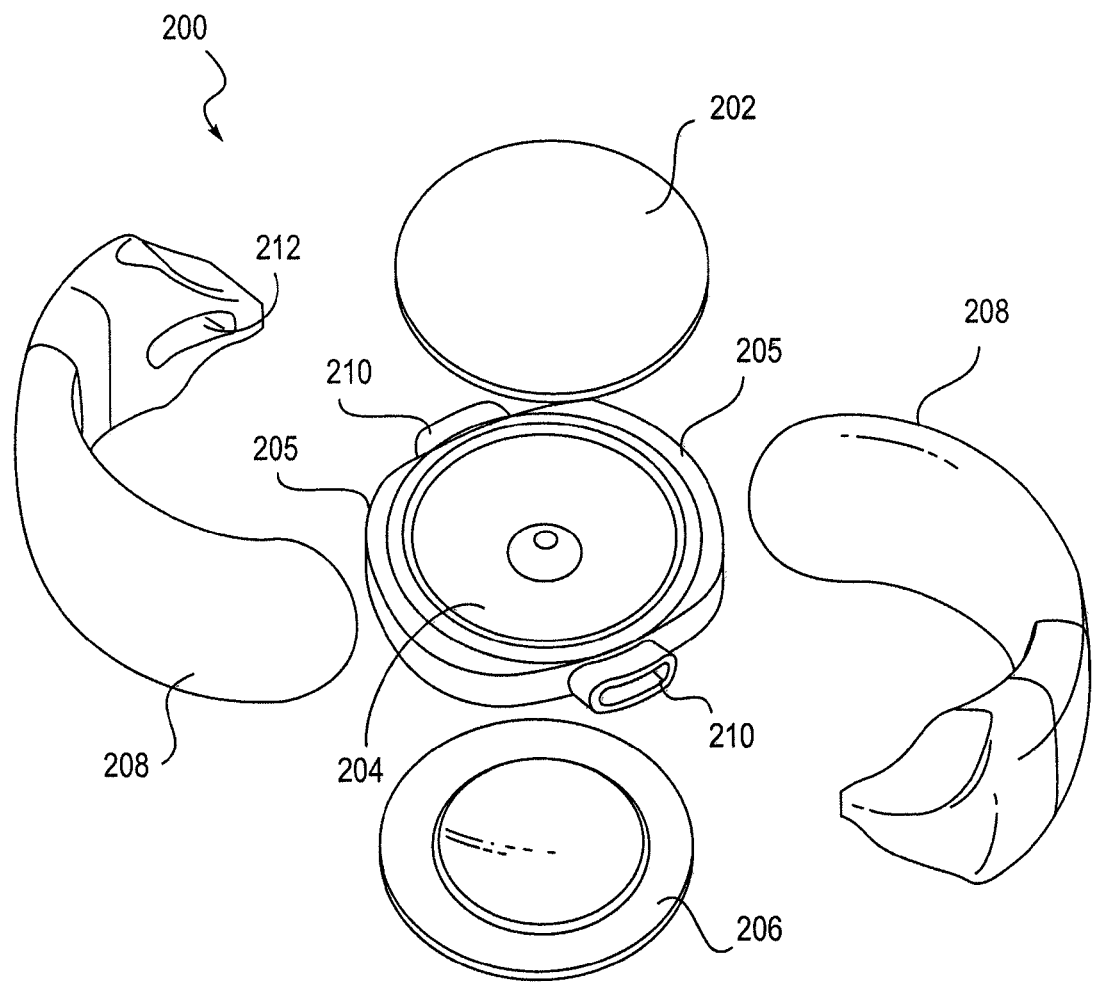
FIGS. 9-12 show an alternative embodiment of an intraocular lens.
Figure 10:
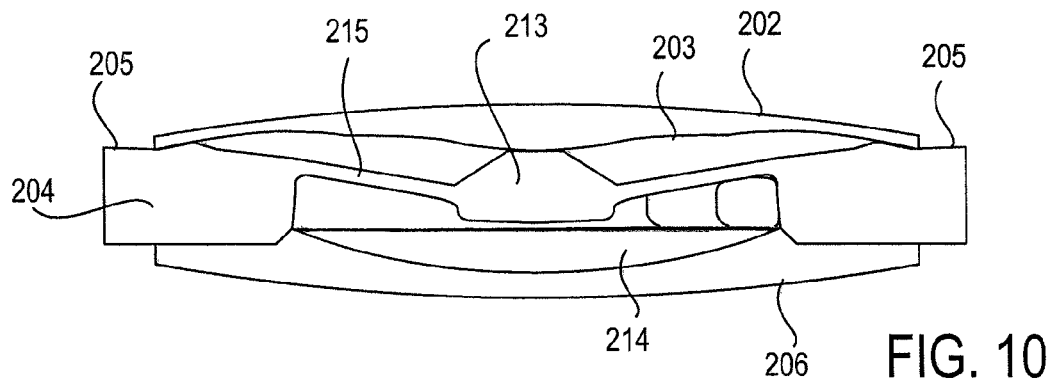
Figure 11:
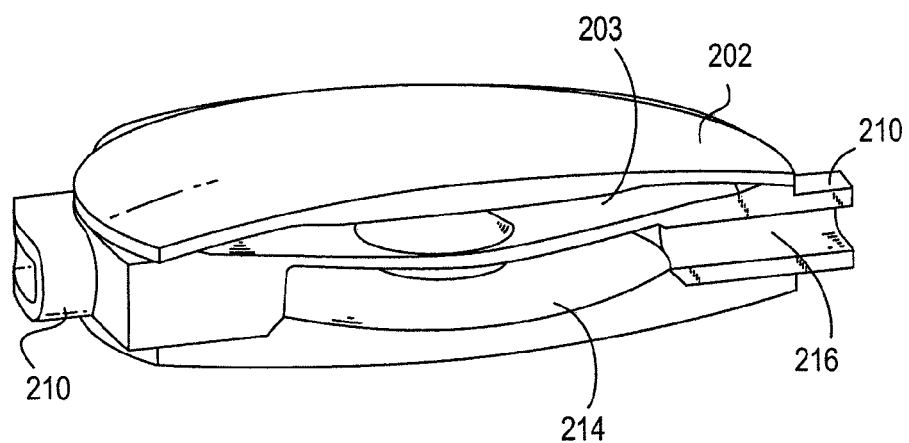

FIGS. 8A-8C show an additional embodiment of IOL 401. IOL 401 includes anterior element 404, intermediate layer 402, posterior element 400, and haptics 412. Intermediate layer 402 comprises an actuator, which comprises deflection element 406 and bellows 408. Also shown are passive chamber 405 and active channel 410. As can be seen in FIGS. 8B and 8C, anterior element 404 and intermediate layer 402 are bonded directly to posterior element 400, which removes an intermediate assembly step of coupling the intermediate layer 402 to the anterior element 404 (as is the construction in the embodiment shown in FIGS. 3-5). Anterior element 404 and intermediate layer 402 are both bonded to posterior element 400 along their periphery. Anterior element 404 is bonded to posterior element 400 at a location more radially outward from the optical axis OA than is intermediate layer 402.

The amount of shape change (i.e., the change in curvature) that the anterior element will undergo in response to fluid movement between the peripheral portion and the optic portion will depend partially on how and where the anterior element is bonded to either the intermediate layer or the posterior element. By varying these boundary conditions it is possible to change the optic power shift for a given amount of displacement at the center of the lens. For example, an anterior element bonded at the very edge of its periphery will deflect in a more spherical manner than will an anterior element that is bonded more radially inward than merely at its periphery. The former is allowed to flex all the way out to its periphery, while the latter is more constrained when deflected and will assume a less spherical configuration when in an accommodated configuration (i.e., will have a stronger aberration).

In addition, the lens bonded at its periphery will deflect at lower active channel pressures than will a lens that is bonded closer to the center.

The anterior element is attached to the posterior element at surface 417 of the posterior element. This mating surface is substantially orthogonal to the optical axis OA. This helps with the assembly process, and gives anterior element 404 a firm foundation on which to sit. FIG. 8C shows a cross sectional perspective view including haptics 412.

The posterior element in FIG. 8A includes buttresses 411. Buttresses 411 include nipples 413 which are adapted to fit within haptic bore 415 to attach the haptics to the posterior element. Adhesive can be applied to the mating surfaces.

Figure 12:
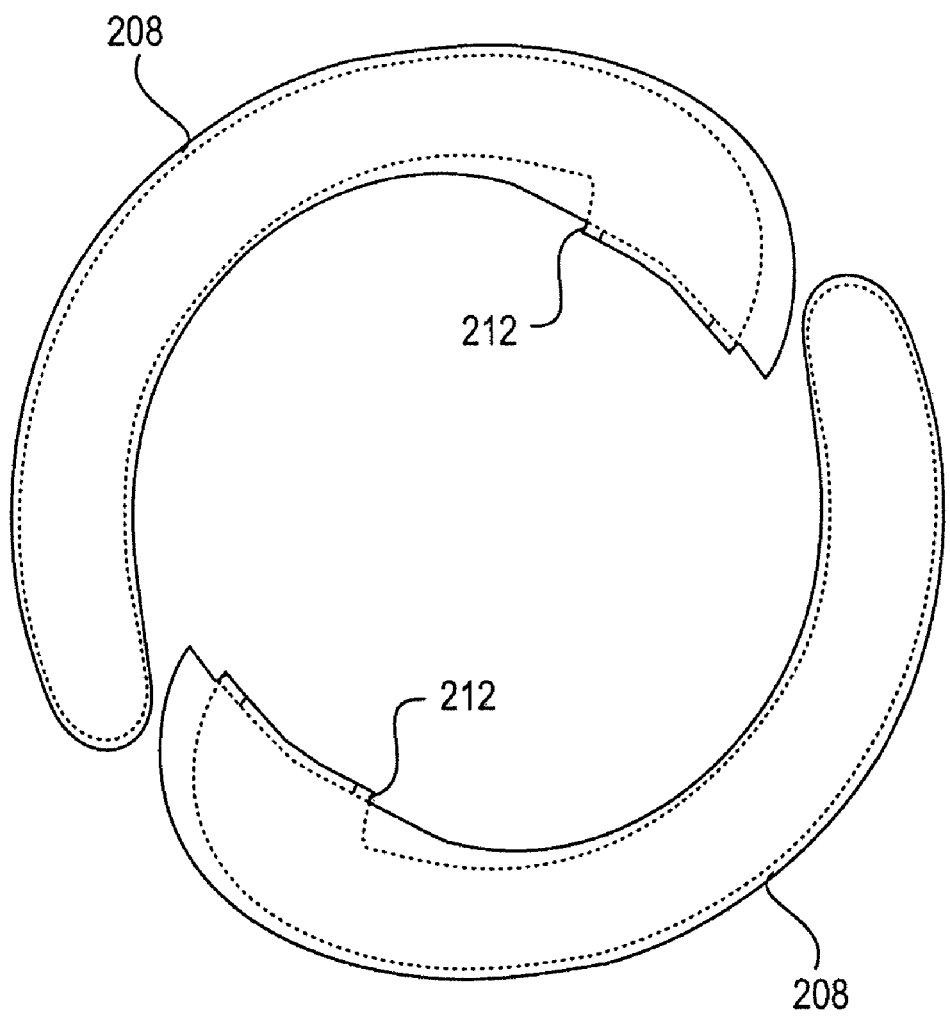

FIGS. 9-12 show an alternative embodiment of IOL 200. IOL 200 includes anterior element 202, intermediate layer 204, posterior element 206, and haptics 208. The haptics are attached to the intermediate layer 204 by attaching buttress elements 212 with optic buttresses 210. The actuator includes deflection element 213 and bellows 215. FIG. 12 is a top view showing the haptics (optic portion not shown). As can be seen, haptic buttress element 212 is incorporated into haptic 208 and attaches to the optic portion at optic buttress 210. One difference in this embodiment is that most of the mechanical complexity is incorporated into one component of the lens—the intermediate layer. Because the haptics incorporate a buttress element, the change in direction (roughly 90 degrees) of the flowable media occurs in the haptic buttress element rather than in an optic buttress as is the case in the embodiments shown in FIGS. 3-5 and FIGS. 8A-8C.

Figure 13:
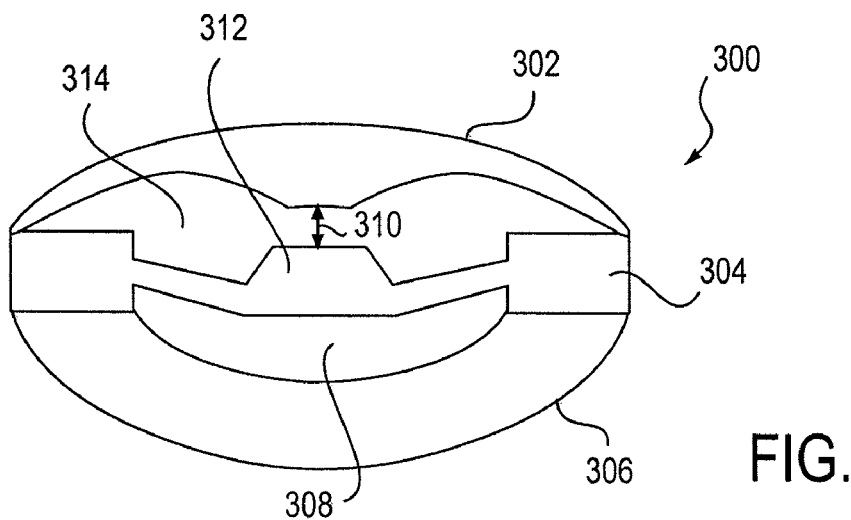
FIGS. 13-15 show an alternative embodiment of an intraocular lens in varying accommodative configurations.
Figure 14:
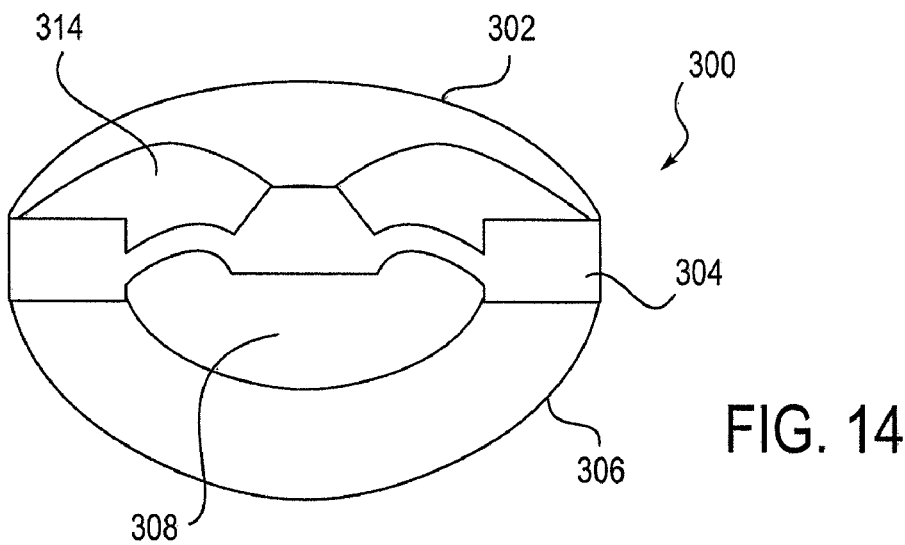
Figure 15:
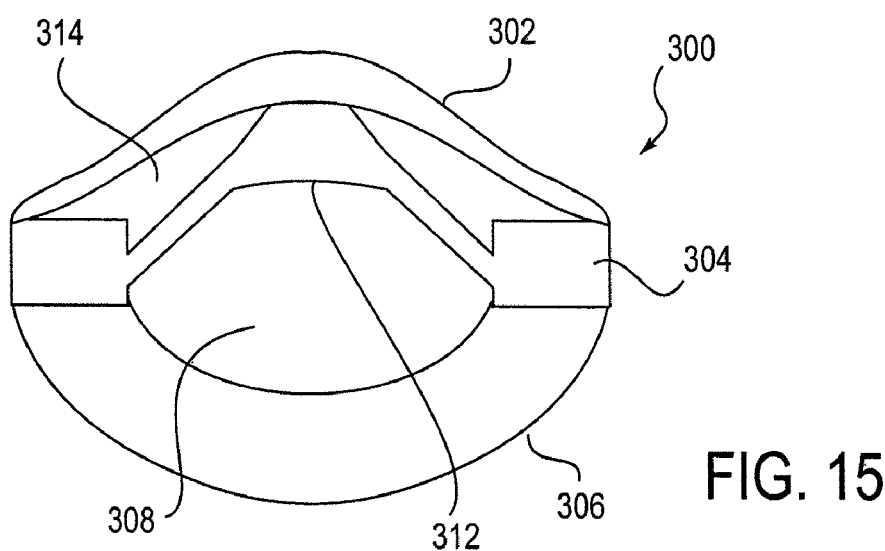

FIGS. 13-15 illustrate an alternative embodiment in which deflection element 312 of the intermediate layer is not in contact with anterior element 302 during the entire accommodation motion of the lens. FIG. 13 shows IOL 300 in a disaccommodated state including anterior element 302, intermediate layer 304 (including deflection element 312 of the actuator), and posterior element 306. The IOL includes gap 310 between the deflection element and the anterior element. When there is no pressure in active channel 308 or in passive chamber 314 (as shown in FIG. 13), the geometry and passive fluid state is such that there is gap 310 between the deflection element and the anterior element.

As the pressure in active channel 308 increases (due to movement of the capsular bag), deflection element 312 moves in the anterior direction. Because of the pressure transfer into passive chamber 314, anterior element 302 also moves in the anterior direction (thus increasing the power of the lens) but remains generally spherical. The deflection element deflects more quickly than the anterior element, until they engage, as shown in FIG. 14.

As the pressure in the active channel continues to increase, the actuator continues to deflect in the anterior direction. Because the deflection element is in contact with the anterior element, further deflection element movement deflects the anterior element. Because of the size of the deflection element relative to the anterior element, the fluid in passive chamber 314 redistributes and creates an aspheric effect in anterior element 302, as shown in FIG. 15. This further increases the power of the IOL for a smaller aperture.

This embodiment allows for a lower power change rate at relatively low stimulus levels (FIG. 14) and a higher power change rate at higher stimulus levels (FIG. 15). The anterior element can remain generally spherical when under a low stimulus and becomes aspherical when under a higher stimulus.

One or more of the optic components can be made from suitable polymeric materials. In one embodiment all of the optic components are made of substantially the same polymeric material. Exemplary polymeric compositions that can be used for the optic portion include those described in commonly owned, co-pending U.S. patent application Ser. No. 12/034,942, filed Feb. 21, 2008, and U.S. patent application Ser. No. 12/177,720, filed Jul. 22, 2008.

The haptics are disposed on the lens such that when implanted in the lens capsule, the haptics deform in response to the capsule shape changes. The capsule changes shape as the zonules apply or relax forces on the capsule in response to ciliary muscle relaxation or contraction.

In one embodiment the IOL is a fluid-driven accommodating IOL which is adapted to move fluid between an interior chamber in the haptics and the optic portion in response to ciliary muscle movement to cause a change in the power of the lens. In a particular embodiment the fluid is moved to the optic portion as the ciliary muscles begin to contract, causing the zonules to relax the forces applied to the capsule. As the zonules relax the forces, the capsule and/or the optic portion compress the haptic, resulting in fluid moving to the optic portion and an increase in fluid pressure in the optic portion. The fluid movement causes a deflection in an anterior element of the lens, which increases the power of the lens.

Figure 16:
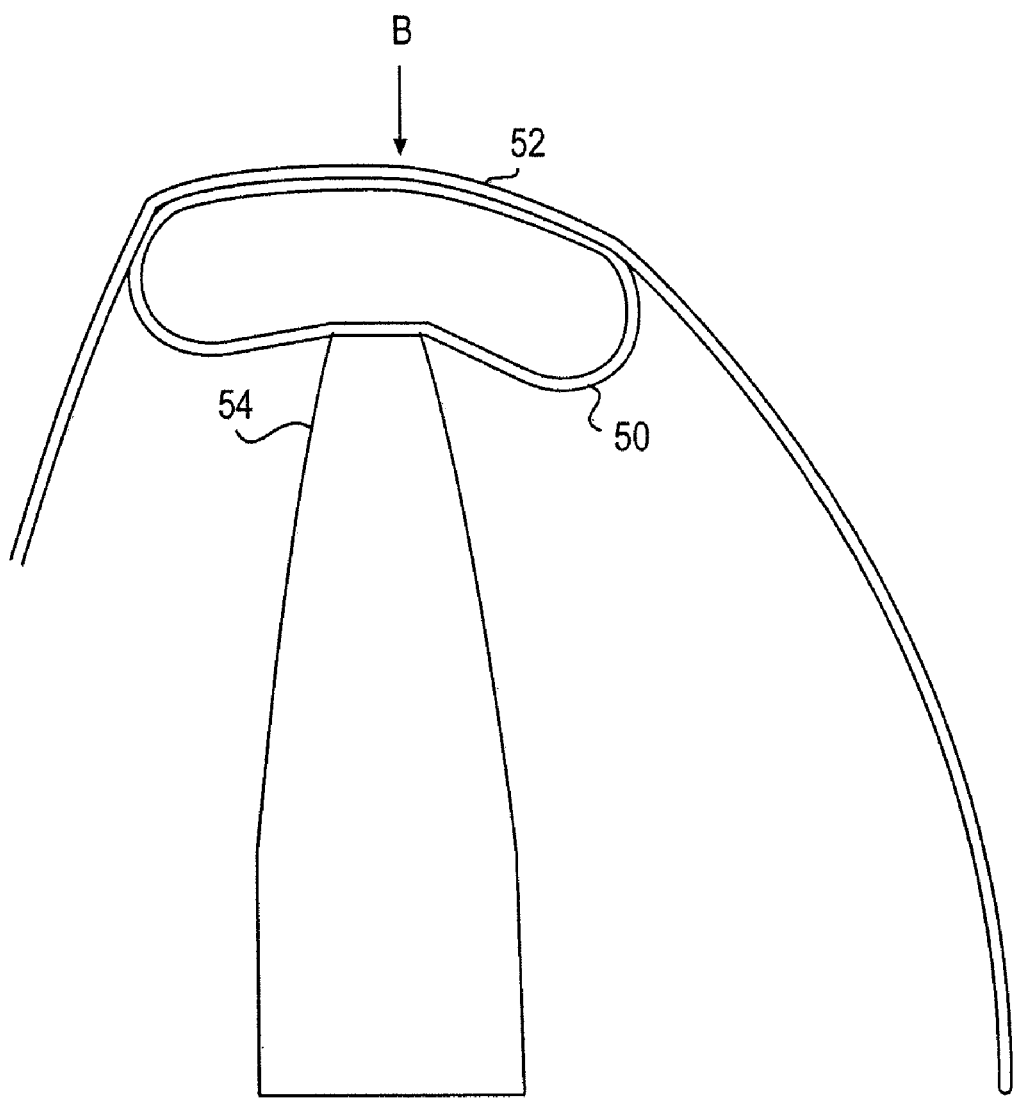
FIG. 16 shows an exemplary haptic being compressed between a lens capsule and an optic portion.

FIG. 16 shows the cross sections of an exemplary haptic 50 being compressed between the lens capsule 52 and the optic portion 54 by compressive force "B". Because the fluid is moved between the haptic and optic portion as the haptic is compressed, the responsiveness of the haptic to the change in forces from the capsule is important in creating an energy efficient IOL. It is generally desirable to transfer energy as efficiently as possible from the forces applied or relaxed on the capsule to the anterior element displacement. The overall shape of the haptic, and perhaps more importantly, the cross-sectional shape of the haptic, can influence how efficiently fluid is transferred between the haptic and the optic portion in response to ciliary muscle relaxation/contraction. It is desirable to obtain a greater response from the haptic in response to a change in force on the lens capsule. It is also desirable to have a haptic/lens system that responds quickly to changes in capsule state.

Figure 17:
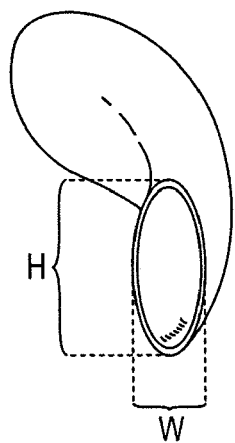
FIGS. 17-20 show exemplary alternative haptic designs.
Figure 19:
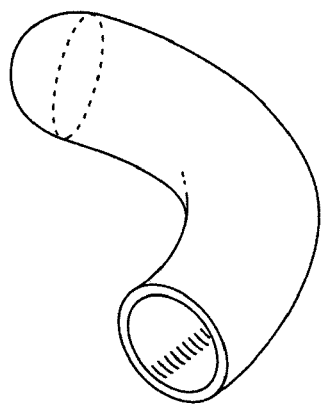
Figure 18:
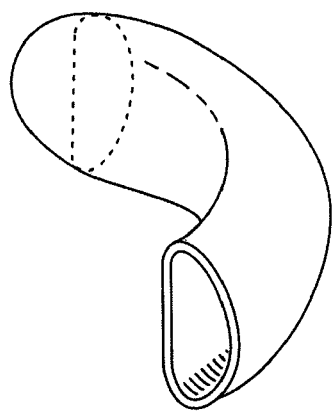
Figure 20:
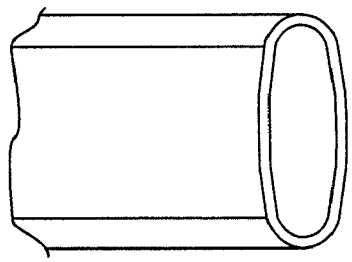

FIGS. 17-20 show exemplary haptic shapes and cross sections. FIG. 17 shows a haptic with an elliptical cross section, with a height H greater than width W. FIG. 18 shows a haptic with a "D" shaped cross section. FIG. 19 shows an alternative haptic shape with a circular cross section. FIG. 20 illustrates a haptic with a flat oval cross section.

Other shapes and/or cross sections can also be used to provide for a more responsive haptic. In addition, the haptic may be comprised of a plurality of sections each with differing polymeric compositions, which may allow one section of the haptic to be stiffer than a different section, which could help increase the responsiveness of the haptic. Exemplary polymeric compositions that can be used for the haptics include those described in U.S. patent application Ser. No. 12/034,942, filed Feb. 21, 2008, and U.S. patent application Ser. No. 12/177,720, filed Jul. 22, 2008.

Figure 21:
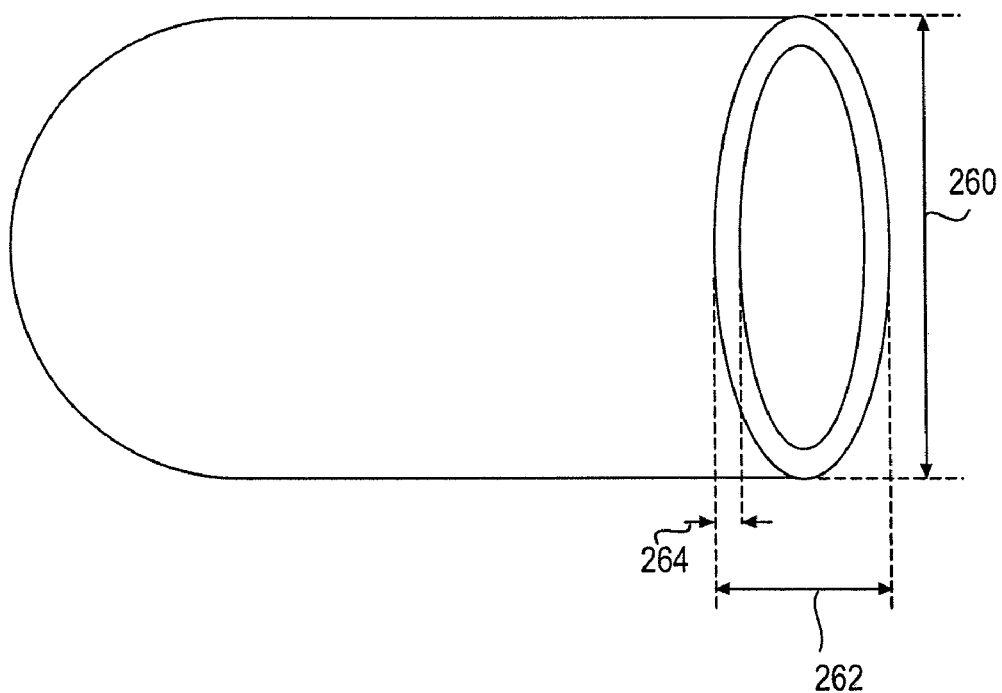
FIG. 21 illustrates dimensions of an exemplary haptic.

Wall thicknesses can also be varied in a given cross-section to allow localized movement and to increase efficiency. FIG. 21 is a cross sectional view showing the exemplary cross section of a haptic. Haptic height 260 is between about 3.0 mm and about 3.4 mm. Haptic width 262 is between about 1.2 mm and about 2.0 mm. Haptic wall thickness 264 is between about 0.1 mm and about 0.3 mm. These dimensions are merely exemplary and are not intended to be limiting.

Figure 22:
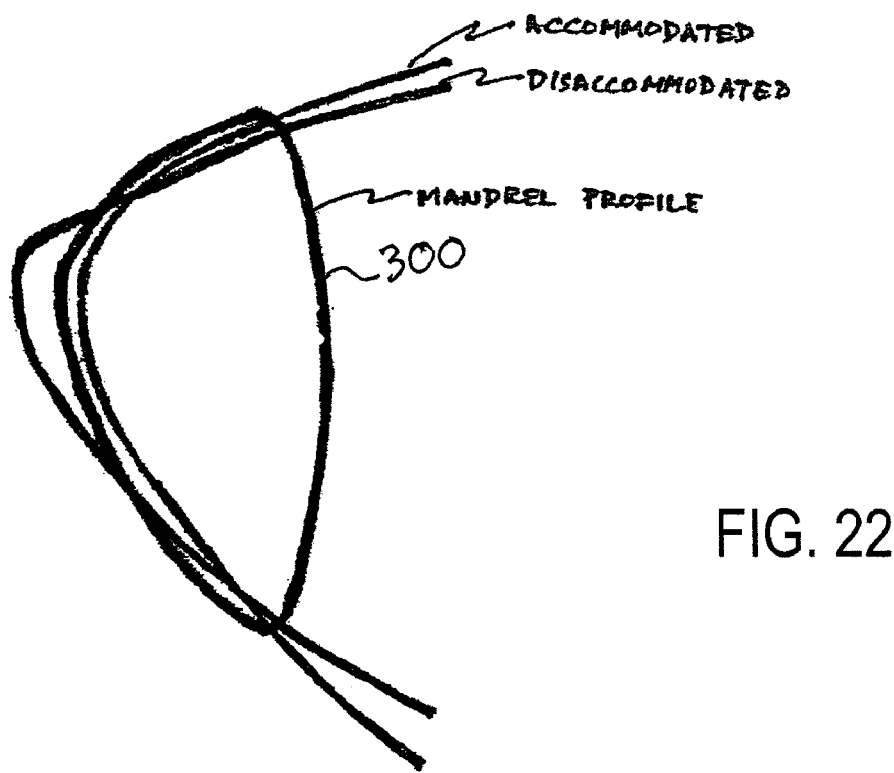
FIG. 22 shows an exemplary haptic design and a capsule in accommodated and disaccommodated configurations.

In some embodiments the haptic shape may be adapted to more naturally mate with the curved equatorial portion of the lens capsule in an disaccommodated state, or to better compliment the corresponding mating surface of the lens. This may help increase the responsiveness of the haptic and decrease the amount of lost movement due to "dead space" between the haptic and the capsule. FIG. 19 is an example of this. FIG. 22 shows an additional cross sectional design of haptic 300, in addition to the capsule in accommodated and disaccommodated configurations.

Figure 23:
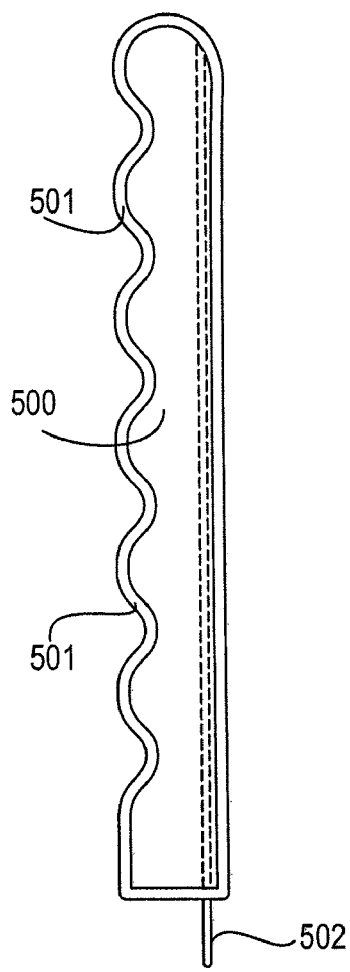
FIGS. 23 and 24 show an alternative haptic design comprising bellows.

FIG. 23 shows an alternative haptic design comprising bellows 501 along one side of haptic 500. The haptic can be attached to the optic portion using any of the methods described or referenced herein. Haptic 500 can also include a reinforcing element 502 along the peripheral side of the haptic to ensure the haptic contacts the capsule bag equator. The reinforcing element can be, for example, a reinforced nitinol wire (metal) or monofilament (plastic).

Figure 24:
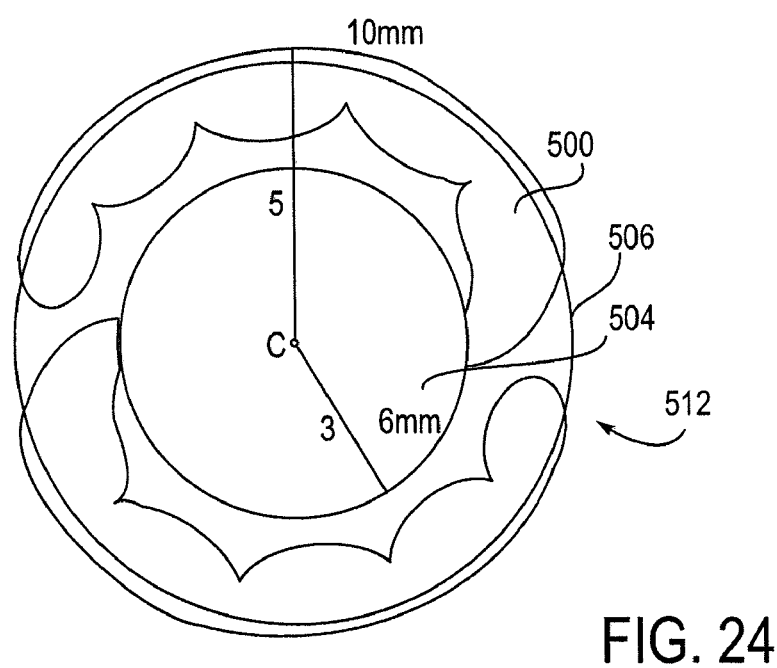

FIG. 24 is a top view showing IOL 512 in a disaccommodated state (natural relaxed state) before implantation relative to exemplary capsular bag 506. Haptics 500 have a diameter of about 10 mm. The optic portion has a diameter of about 6 mm. When implanted in the capsular bag, the capsular bag relaxation causes pressure to be exerted on the haptics, thus bending the haptics. The bellows provide for greater volume reduction in the haptics, which displaces more volume of fluid to the optic portion.

Additional exemplary accommodating IOLs that can incorporate any of the features described herein are described in commonly owned U.S. Provisional Application No. 60/433,046, filed Dec. 12, 2002; U.S. Pat. Nos. 7,122,053; 7,261,737; 7,247,168; and 7,217,288; U.S. patent application Ser. No. 11/642,388, filed Dec. 19, 2006; and U.S. patent application Ser. No. 11/646,913, filed Dec. 27, 2006, the disclosures of which are hereby incorporated by reference in their entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of changing an optical parameter of an accommodating intraocular lens; comprising:

implanting an intraocular lens comprising an optic portion and a peripheral portion extending peripherally from the optic portion, wherein the optic portion comprises an optical axis extending in an anterior to posterior direction and passing through the center of the optic portion, an anterior element, a posterior element, and a flexible intermediate layer disposed between the anterior element and the posterior element, the optical axis passing through the flexible intermediate layer, wherein the flexible intermediate layer partially defines a channel in the optic portion that is in communication with the peripheral portion, wherein a flowable media is disposed in the channel in the optic portion and is capable of moving between the channel in the optic portion and the peripheral portion; and moving the flowable media between the channel in the optic portion and the peripheral portion in response to ciliary muscle movement to change an optical parameter of the intraocular lens, wherein moving the flowable media between the optic portion and the peripheral portion comprises moving the intermediate layer and at least one of the anterior element and the posterior element from a first configuration to a second configuration.

2. The method of claim 1 wherein moving a flowable media between the optic portion and the peripheral portion comprises deforming the peripheral portion.

3. The method of claim 1 wherein moving the intermediate layer and at least one of the anterior element and the posterior element comprises moving the intermediate element and the anterior element.

4. The method of claim 1 wherein the anterior element, the flexible intermediate layer, the posterior element, and the flowable media in the optic portion all have substantially the same index of refraction.

5. The method of claim 1 wherein the flexible intermediate layer and the posterior element define the channel in the optic portion that is in communication with the peripheral portion.

6. The method of claim 1 wherein moving the intermediate layer and at least one of the anterior element and the posterior element comprises moving the intermediate layer and the posterior layer.

7. The method of claim 1 further comprising redistributing a second flowable media within a passive chamber within the optic portion.

* * * * *

UNITED STATES PATENT AND TRADEMARK OFFICE
CERTIFICATE OF CORRECTION

| | | |
|---|---|---|
| PATENT NO. | : 8,328,869 B2 | Page 1 of 1 |
| APPLICATION NO. | : 12/177857 | |
| DATED | : December 11, 2012 | |
| INVENTOR(S) | : Smiley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-eighth Day of October, 2014

Michelle K. Lee
*Deputy Director of the United States Patent and Trademark Office*